United States Patent [19]

Dusza et al.

[11] Patent Number: 4,551,530
[45] Date of Patent: Nov. 5, 1985

[54] PYRIDYL IMIDAZO[1,2-A]PYRIMIDINES

[75] Inventors: John P. Dusza; Jay D. Albright, both of Nanuet, N.Y.

[73] Assignee: American Cyanamid Company, Stamford, Conn.

[21] Appl. No.: 672,753

[22] Filed: Nov. 19, 1984

[51] Int. Cl.$^4$ ............... C07D 487/04; A61K 31/505
[52] U.S. Cl. .................................................. 544/281
[58] Field of Search ........................................ 548/281

[56] References Cited

U.S. PATENT DOCUMENTS

| | | |
|---|---|---|
| 2,785,133 | 3/1957 | Craig .................................. 544/281 |
| 4,236,005 | 11/1980 | Dusza et al. ........................ 544/281 |
| 4,374,988 | 2/1983 | Dusza et al. ........................ 544/281 |

FOREIGN PATENT DOCUMENTS 76677  10/1970  Fed. Rep. of Germany ...... 544/281

Primary Examiner—Donald G. Daus
Assistant Examiner—S. A. Gibson
Attorney, Agent, or Firm—Anne M. Rosenblum; Susan H. Rauch

[57] ABSTRACT

A compound of the formula:

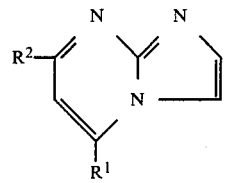

wherein $R_1$ is 3-pyridyl or 4-pyridyl; and $R_2$ is hydrogen or lower alkyl ($C_1$–$C_3$); or a nontoxic pharmaceutically acceptable salt thereof.

2 Claims, No Drawings

PYRIDYL IMIDAZO[1,2-A]PYRIMIDINES

SUMMARY OF THE INVENTION

This invention relates to novel pyridyl imidazo[1,2-a]pyrimidines, represented by the following formula I:

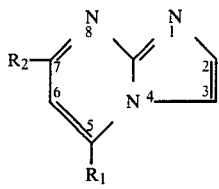

wherein $R_1$ is 3-pyridyl or 4-pyridyl; and $R_2$ is hydrogen or lower alkyl ($C_1$–$C_3$); or a nontoxic pharmaceutically acceptable salt thereof. The invention further concerns the use of these novel compounds as antihypertensive or anxiolytic agents and the process of preparing them.

DETAILED DESCRIPTION OF THE INVENTION

In accordance with the present invention, there are provided novel compounds represented by the following generic formula I:

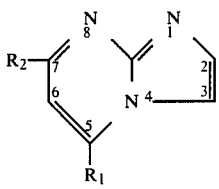

wherein $R_1$ is 3-pyridyl or 4-pyridyl; and $R_2$ is hydrogen or lower alkyl ($C_1$–$C_3$); or a nontoxic pharmaceutically acceptable salt thereof.

Particularly preferred compounds of formula I which are of major interest as antihypertensive agents include the following:

5-(3-Pyridyl)imidazo[1,2-a]pyrimidine
5-(4-Pyridyl)imidazo[1,2-a]pyrimidine
5-(4-Pyridyl)imidazo[1,2-a]pyrimidine,hydrochloride
7-Methyl-5-(3-pyridinyl)imidazo[1,2-a]pyrimidine
7-Methyl-5-(4-pyridinyl)imidazo[1,2-a]pyrimidine A particularly preferred compound of formula I which is of major interest as an anxiolytic agent includes 5-(3-pyridyl)imidazo[1,2-a]pyrimidine.

This invention further deals with a method of lowering elevated blood pressure in a mammal which comprises administering to said mammal an effective hypotensive amount of a compound of formula I, wherein $R_1$ and $R_2$ are as above defined. The invention also concerns a method of alleviating anxiety in a mammal which comprises administering to said mammal an effective antianxiety amount of a compound of formula I, wherein $R_1$ is 3-pyridyl and $R_2$ is hydrogen; or a nontoxic pharmaceutically acceptable salt thereof. Moreover, the instant invention includes novel therapeutic compositions containing the above-identified compounds.

The novel compounds of the present invention are in general obtainable as colorless, yellow or tan crystalline solids having characteristic melting points and absorption spectra. The bases are appreciably soluble in many organic solvents such as lower alkanols, chloroform, dichloromethane, tetrahydrofuran, N,N-dimethylformamide and the like, but are relatively insoluble in water. The organic bases of the present invention form nontoxic acid-addition salts with a variety of pharmacologically acceptable organic and inorganic salt forming reagents. Thus, the term "nontoxic pharmaceutically acceptable salt" refers to the acid-addition salts, formed by admixture of the organic free base with one or two equivalents of an acid, preferably in a neutral solvent. Suitable acids include, but are not limited to, sulfuric, phosphoric, hydrochloric, hydroiodic, sulfamic, citric, lactic, fumaric, succinic, tartaric, acetic, benzoic, gluconic, ascorbic and the like. For purposes of this invention, the free bases equivalent to their nontoxic acid-addition salts.

The compounds of the instant invention may be readily prepared in accordance with the following reaction scheme:

REACTION SCHEME

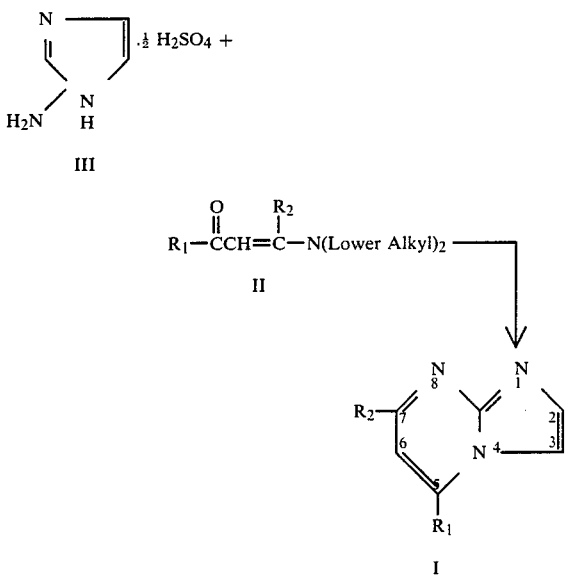

wherein $R_1$ is 3-pyridyl or 4-pyridyl; and $R_2$ is hydrogen or lower alkyl($C_1$–$C_3$). As shown above, 2-aminoimidazole hemisulfate (III) is condensed with an appropriately substituted 3-di (lower alkyl) aminoacrylophenone (II) in the presence of anhydrous sodium acetate, in an inert organic solvent such as a lower alkanol, dioxane, tetrahydrofuran, toluene and the like, with or without acid catalysis. The preferred procedure is the reaction of II with III in refluxing glacial acetic acid for 0.5–16 hours to provide the compounds (I) of the invention.

The intermediate compounds (II), where $R_1$ is 3- or 4-pyridyl and $R_2$ is lower alkyl ($C_1$–$C_3$), are prepared by heating a mixture of methylheteroaryl ketone such as 3-acetylpyridine or 4-acetylpyridine in dimethylacetamide dimethylacetal for 2 to 16 hours in an inert atmosphere, then evaporating the solvent in vacuo and crystallizing the product with the aid of a solvent such as hexane.

The novel compounds of the present invention are active hypotensive agents at nontoxic doses when administered to mammals. These compounds were tested for hypotensive activity by the method of P. S. Chan and D. W. Poorvin, Clinical and Experimemtal Hypertension, 1 (6):817–830 (1979). Male, 16 week-old, spontaneously hypertensive rats of the Okamoto strain, from Taconic Farms, Germantown, New York, having an average mean arterial blood pressure of 160±1.5 mm of mercury are used in the test. A rat weighing about 300 g is dosed by gavage with a test compound, suspended in 2% pre-boiled starch at a concentration of 50 mg/ml, at a dose of 100 mg/kg of body weight, with 0.9% sodium chloride loading at a dose of 25 ml/kg of body weight. A second identical dose of the test compound, without sodium chloride loading, is given 24 hours later. At 28 hours after the initial dose the mean arterial blood pressure (MABP) is measured by the method of Chan and Poorvin vide supra. A test compound is considered active if it lowers the elevated blood pressure by 25 mm Hg or more. The results of this test on representative compounds of the present invention appear below in Table I.

TABLE I

Reduction of Mean Arterial Blood Pressure in Spontaneously Hypertensive Rats

| Compound | MABP/mm Hg (No. of Rats) |
|---|---|
| 5-(3-Pyridyl)imidazo[1,2-a]pyrimidine | 123(1) |
| 5-(4-Pyridyl)imidazo[1,2-a]pyrimidine | 104(1) |
| 5-(4-Pyridyl)imidazo[1,2-a]pyrimidine, hydrochloride | 109(2) |
| 7-Methyl-5-(3-pyridinyl)imidazo[1,2-a]pyrimidine | 108(1) |
| 7-Methyl-5-(4-pyridinyl)imidazo[1,2-a]pyrimidine | 78(1) |

The novel compounds of the present invention also possess central nervous system activity at nontoxic doses and as such are useful as anxiolytic agents. They produce certain responses in standard tests with laboratory animals which are known to correlate well with relief of anxiety in human beings. The compounds, when tested pharmacologically, are found to have a desirable wide spread between doses producing anxiolytic activity and toxic symptoms.

The antianxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle containing 0.5% v/v polyethylene glycol and one drop of polysorbate 80, or distilled water and one drop of polysorbate 80 to groups of at least 4 rats. At 30 or 60 minutes, the rats were treated intravenously with pentylenetetrazole at a dose of 23 mg/kg of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology," pp. 237–288 (Eds. R. R. Rech and K. E. Moore, Raven Press, New York, 1971)] that there is a high degree of correlation between antagonism of pentylenetetrazole seizures in rats and antianxiety effects in higher warm-blooded animals. The result of this in vivo test on a representative compound of the present invention is shown in Table II.

TABLE II

Protection Against Clonic Seizures Caused by Pentylenetetrazole in Rats

| Compound | Dose (mg/kg) | % of Rats Protected |
|---|---|---|
| 5-(3-Pyridyl)imidazo[1,2-a]pyrimidine | 50 | 75 |

Another test used to assess antianxiety effects is a non-conditioned passive avoidance procedure described by J. R. Vogel, B. Beer and D. E. Clody. "A Simple and Reliable Conflict Procedure for Testing Antianxiety Agents," Psychopharmacologia, 21:1–7 (1971). A conflict situation is induced in rats by a modification of this method.

Groups of 8 naive, Wistar strain male rats weighing 200–240 g each were deprived of water for 48 hours. The test compounds were administered in single or graded, oral doses, suspended in distilled water and one drop of polysorbate 80. Control animals received the vehicle alone. At 30 or 60 minutes each rat was placed in an individual clear plexiglass chamber. Tap water was available ad libitum from a nipple located in a black plexiglass box off the main chamber. A 0.7 milliampere AC shocking current was established between the stainless steel grid floor and the tap. After 20 licks of non-shocked drinking, a 2 second shocking current was administered to the rat. This ratio of 20 licks of non-shocked drinking followed by a 2 second shock was continued for a total of 3 minutes. The number of shocks taken by each rat during the 3 minute interval was recorded and compared to a control group. The test compounds are considered active if the number of shocks received by the test group is significantly higher than the control group by the Mann-Whitney U test. That is, the test compounds are considered active if they result in the treated rat taking slightly more than double the number of shocks that the untreated rat will take. Results of this in vivo test on a representative compound of the present invention are given in Table III.

TABLE III

Conflict Procedure In Rats

| Compound | Dose (mg/kg) | Result (No. of Shocks per 3 min.) |
|---|---|---|
| 5-(3-Pyridyl)imidazo[1,2-a]pyrimidine | 25.0 | 15–20 |
| Control Group | — | 6 |

Still another test utilized for the determination of anxiolytic activity is the measurement of the ability of a test compound to inhibit the binding of tritiated benzodiazepines to brain-specific receptors of mammals. A modification of the method described by R. F. Squires, et al., Nature, 266, No. 21:732 (April, 1977) and H. Mohler, et al., Science, 198:849 (1977) was employed. Male albino rats (Wistar strain, weighing 150–200 g each) were obtained from Royalhart Farms. $^3$H-methyldiazepam (79.9 Ci/mmol) and $^3$H-methyl-flunitrazepam (84.3 Ci/mmol) were obtained from New England Nuclear. The test compounds were solubilized in dimethylformamide, acetic acid, ethanol or hydrochloric acid.

Whole cortex of rats was homogenized gently in 20 volumes of ice-cold 0.32 M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen (−20° C.) until time of use. Frozen $P_2$ preparations were thawed and resuspended in four times the original homogenizing volume at time of assay.

The binding assay consisted of 300 μl of the $P_2$-fraction suspension (0.2–0.4 mg protein), 100 μl of test drug and 100 μl of $^3H$-diazepam (1.5 nM, final concentration) or $^3H$-flunitrazepam (1.0 nM, final concentration) which was added to 1.5 ml of 50 nM Tris.HCl (pH 7.4). Non-specific binding controls and total binding controls received 100 μl of diazepam (3 μM final concentration) and 100 μl of deionized water, respectively, in place of the test compound. Incubation for 30 minutes proceeded in ice and was terminated by filtration, under vacuum, through Whatman GF/C glass fiber filters TM (a specific receptor for filtration by binding, registered trademark of Whatman Inc., Clifton, NJ 07014). The filters were washed twice with 5 ml of ice-cold 50 mM Tris.HCl (pH 7.4) and placed in scintillation vials. After drying at 50°–60° C. for 30 minutes, 10 ml of Beckman Ready-Solve TM HP (a high performance pre-mix scintillation cocktail, registered trademark of Beckman Instruments, Inc., Irvine, CA 92713) was added and the radioactivity determined in a scintillation counter.

Inhibition of binding was calculated by the difference between total binding and binding in the presence of test compound, divided by the total binding, X 100. Physiological activity can be shown by a test compound that inhibits $^3H$-benzodiazepine binding by 12% or more. Such in vitro activity is biologically relevant when the test compound also demonstates statistically significant anxiolytic activity through in vivo studies.

The result of this in vitro test on a representative compound of this invention is given in Table IV.

TABE IV

| Inhibition of the Binding of $3_H$-Benzodiazepine to Brain-Specific Receptors of Rats | |
| --- | --- |
| Compound | % Inhibition |
| 5-(3-Pyridyl)imidazo[1,2-a]pyrimidine | 12 |

The novel compounds of the present invention have been found to be highly useful for lowering elevated blood pressure in mammals when administered in amounts ranging from about 25 mg to about 100 mg per kilogram of body weight per day. A preferred dosage regimen for optimum results would be from about 50 mg to about 750 mg per dose. Such dosage units are employed that a total of from about 200 mg to about 3.0 g of the active compound for a subject of about 70 kg of body weight are administered in a 24 hour period.

The novel compounds of the present invention which are effective for alleviating anxiety in warm-blooded animals are administered in amounts ranging from about 0.1 mg to about 35.0 mg per kilogram of body weight per day. A preferred dosage regimen for optimum results would be from about 0.5 mg to about 20.0 mg per kilogram of body weight per day, and such dosage units are employed that a total from about 35 mg to about 1.4 g of the active compound for a subject of about 70 kg of body weight are administered in a 24 hour period.

The dosage regimen for the above-described utilities may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by oral, intravenous, intramuscular or subcutaneous routes.

The active compounds may be orally administered, for example, with an inert diluent or with an assimilable edible carrier. They may be enclosed in hard or soft shell gelatin capsules or compressed into tablets. They may also be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as sodium lauryl sulfate or an emulsifier or stabilizer such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be described in greater detail in conjunction with the following non-limiting examples.

EXAMPLE 1

5-(3-Pyridyl)imidazo[1,2-a]pyrimidine

A mixture of 5.29 g of 2-aminoimidazole hemisulfate, 3.28 g of anhydrous sodium acetate and 7.04 g of 3-dimethylamino-1-(3-pyridyl)-2-propen-1-one (prepared according to the procedure of Example 1 in U.S. Pat. No. 4,281,000) in 100 ml of glacial acetic acid was heated under reflux for 16 hours. The solvent was removed in vacuo. The solid residue was made basic with saturated aqueous sodium bicarbonate, then was extracted with dichloromethane. The dichloromethane solution was passed through a short column of a hydrous magnesium silicate. The effluent was refluxed on a steam bath with the gradual addition of hexane until crystallization was noted. On cooling, the desired compound was separated and collected by filtration and gave 2.54 g of yellow prisms, mp 162°–164° C.

EXAMPLE 2

5-(4-Pyridyl)imidazo[1,2-a]pyrimidine

A mixture of 5.29 g of 2-aminoimidazole hemisulfate, 3.28 g of anhydrous sodium acetate and 7.04 g of 3-dimethylamino-1-(4-pyridyl)-2-propen-1-one (prepared according to the procedure of Example 63 in U.S. Pat. No. 4,281,000) in 100 ml of glacial acetic acid was heated under reflux for 16 hours. The procedure of the above Example 1 was followed and the title compound was obtained as pale yellow needles, mp 244°–245° C.

EXAMPLE 3

5-(4-Pyridyl)imidazo[1,2-a]pyrimidine, hydrochloride

A 2.0 g amount of 5-(4-pyridyl)imidazo[1,2-a]pyrimidine was suspended in 100 ml of triethylorthoformate and 1.67 ml of concentrated hydrochloric acid was added. After standing at room temperature for 6 hours the resultant precipitate was collected by filtration and gave 0.47 g of the product of the Example as a yellow solid, mp 295°–300° C.(dec.).

EXAMPLE 4

3-(Dimethylamino)-1-(3-pyridinyl)-2-buten-1-one

A mixture of 40.0 g of 3-acetylpyridine and 50.0 ml of dimethylacetamide dimethylacetal was heated on a steam bath for 6 hours under argon. The volatile components were then removed in vacuo and hexane was added to the resultant thick syrup to crystallize the product. Filtration gave 33.5 g of the desired product as red-brown crystals, mp 62°–64° C.

EXAMPLE 5

3-(Dimethylamino)-1-(4-pyridinyl)-2-buten-1-one

When 4-acetylpyridine was substituted for 3-acetylpyridine in the procedure of Example 4, the product of the Example was obtained as yellow brown crystals, mp 88°–89° C.

The compounds of the following Examples 6 and 7 in Table V were prepared by the procedure described in Example 1 using the title compounds of Examples 4 and 5, respectively, as the starting material.

TABLE V (Pyridyl)imidazo [1,2-a]pyrimidines $$\text{structure} + \frac{1}{2}H_2SO_4 + R_1-\overset{O}{\overset{\|}{C}}CH=\overset{R_2}{\underset{|}{C}}-N(CH_3)_2 \longrightarrow \text{product}$$

| Example | Compound | $R_1$ | $R_2$ | Description | MP °C. |
|---|---|---|---|---|---|
| 6 | 7-Methyl-5-(3-pyridinyl)imidazo-[1,2-a]pyrimidine | 3-pyridyl | $CH_3$ | Very pale yellow needles | 180–181 |
| 7 | 7-Methyl-5-(4-pyridinyl)imidazo-[1,2-a]pyrimidine | 4-pyridyl | $CH_3$ | Very pale yellow crystals | 208–210 |

We claim:

1. The compound, 5-(3-pyridyl)imidazo[1,2-a]pyrimidine or a nontoxic pharmaceutically acceptable salt thereof.

2. The compound, 5-(4-pyridyl)imidazo[1,2-a]pyrimidine or a nontoxic pharmaceutically acceptable salt thereof.

* * * * *